United States Patent
Nishikiori et al.

(10) Patent No.: US 8,394,636 B2
(45) Date of Patent: *Mar. 12, 2013

(54) REMOTE CONTROL METHOD, REMOTE CONTROL SYSTEM, STATUS INFORMING DEVICE AND CONTROL APPARATUS

(75) Inventors: Mizuho Nishikiori, Kobe (JP); Tadayuki Yamaguchi, Kobe (JP); Hiroshi Murakami, Kobe (JP)

(73) Assignee: Sysmex Corporation, Kobe (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/414,845

(22) Filed: Mar. 8, 2012

(65) Prior Publication Data

US 2012/0173618 A1 Jul. 5, 2012

Related U.S. Application Data

(63) Continuation of application No. 13/073,703, filed on Mar. 28, 2011, now Pat. No. 8,158,431, which is a continuation of application No. 11/218,202, filed on Aug. 31, 2005, now Pat. No. 7,998,741.

(30) Foreign Application Priority Data

Aug. 31, 2004 (JP) .................................. 2004-252763

(51) Int. Cl.
*G01N 33/00* (2006.01)

(52) U.S. Cl. ......................................... 436/43; 422/500

(58) Field of Classification Search .................... 436/43; 422/500
See application file for complete search history.

(56) References Cited

U.S. PATENT DOCUMENTS

| | | | |
|---|---|---|---|
| 5,353,238 A | 10/1994 | Neef et al. | |
| 6,629,060 B2 | 9/2003 | Okuno et al. | |
| 7,998,741 B2 * | 8/2011 | Nishikiori et al. | 436/43 |
| 8,158,431 B2 * | 4/2012 | Nishikiori et al. | 436/43 |
| 2002/0067372 A1 | 6/2002 | Friedrich et al. | |
| 2003/0021734 A1 | 1/2003 | Vann et al. | |
| 2003/0036832 A1 | 2/2003 | Kokes et al. | |

FOREIGN PATENT DOCUMENTS

| | | |
|---|---|---|
| EP | 0893772 A2 | 1/1999 |
| EP | 0943972 A1 | 9/1999 |
| JP | 2002-091913 A | 3/2002 |
| JP | 2002-268721 A | 9/2002 |
| WO | WO 98/33102 A1 | 7/1998 |

OTHER PUBLICATIONS

European Search Report for European Application No. 05018775, dated Nov. 8, 2005, 2 pages.
Office Action from counterpart Japanese Application No. 2004-252763, dated Sep. 22, 2010, 26 pages.

* cited by examiner

*Primary Examiner* — Sam P Siefke
(74) *Attorney, Agent, or Firm* — Brinks Hofer Gilson & Lione

(57) ABSTRACT

The objective of the present invention is to provide a remote control method which allows a technician, etc. in a support center to remote-control a clinical specimen processing device, and a remote control system, a status informing device and a control apparatus used for such a method. The remote control method of the present invention, which is a remote control method for remote-controlling the clinical specimen processing device that processes a clinical specimen, is designed so that an image of the clinical specimen processing device is picked up by an image pickup device, and the image picked up by the image pickup device is supplied to a control apparatus located at a remote place from the clinical specimen processing device through a communication network so that the picked-up image is displayed on the control apparatus.

20 Claims, 12 Drawing Sheets

REMOTE CONTROL METHOD, REMOTE CONTROL SYSTEM, STATUS INFORMING DEVICE AND CONTROL APPARATUS

This application is a continuation application of U.S. patent application Ser. No. 13/073,703, filed Mar. 28, 2011 now U.S. Pat. No. 8,158,431, which is a continuation of U.S. patent application Ser. No. 11/218,202, filed Aug. 31, 2005 now U.S. Pat. No. 7,998,741, which claims priority under 35 U.S.C. §119 to Japanese Patent Application No. 2004-252763, filed Aug. 31, 2004, the entire contents of which are hereby incorporated by reference.

FIELD OF THE INVENTION

The present invention relates to a remote control method that remote-controls a clinical specimen processing device used for processing a clinical specimen, a remote control system used for the remote control method and a status informing device and a control apparatus that are installed in the remote control system.

BACKGROUND

Clinical specimen processing devices for processing clinical specimens, such as a blood smear sample forming device for preparing a smear sample of a blood specimen, a blood analyzing device for analyzing a blood specimen, a urine analyzing device for analyzing a urine specimen and a stool analyzing device for analyzing a stool specimen, have been widely known. In the event of an error in such a clinical specimen processing device, it is necessary to inform the user or a support center or the like that carries out technical support on the device of the corresponding error. For this reason, a technique by which the occurrence of an error is informed to the support center or the like has been proposed (for example, see U.S. Pat. No. 6,629,060).

The above-mentioned U.S. Pat. No. 6,629,060 has disclosed a method in which: an analyzing device and a control apparatus are connected to each other through a network, and the analyzing device transmits history information that shows the operation history of the analyzing device to a control apparatus by using an electronic mail so that the control apparatus stores pieces of the history information for respective analyzing devices. With this arrangement, the technician in the support center is allowed to confirm the stored history information through the control apparatus so that the technician is allowed to recognize the state of the analyzing device without the necessity of asking for a detailed explanation about the analyzing device from the user; thus, it becomes possible to easily carry out the failure recovering operation.

However, in most cases, the above-mentioned clinical specimen processing devices have complex structures, and it sometimes becomes difficult to confirm the state of the device in detail by examining only the history information. In such a case, the support center needs to dispatch a technician to the user's facility or the like in which the clinical specimen processing device is installed, and make the technician examine the status of the clinical specimen processing device on the spot; therefore, much time and time-consuming tasks are required for the failure recovering operation.

BRIEF SUMMARY

The scope of the present invention is defined solely by the appended claims, and is not affected to any degree by the statements within this summary.

The present invention has been devised to solve the above-mentioned problems, and its objective is to provide a remote control method in which an image of a clinical specimen processing device is transmitted to a control apparatus that is placed far away from the clinical specimen processing device through a communication network so that a technician, etc. of the support center is allowed to confirm a detailed state of the clinical specimen processing device without the necessity of having to go to the installation position of the clinical specimen processing device, a remote control system to be used for the remote control method, and a status informing device and a control apparatus that are installed in the remote control system.

The first aspect of the present invention relates to a remote control method, which remote-controls a clinical specimen processing device for processing a clinical specimen, comprising the steps of: picking up an image of the clinical specimen processing device; supplying the picked-up image to a control apparatus placed at a remote place from the clinical specimen processing device through a communication network; and displaying the picked-up image on the control apparatus.

The second aspect of the present invention relates to a remote control system comprising: a clinical specimen processing device that processes a clinical specimen; an image pickup device used for picking up an image of the clinical specimen processing device; a control apparatus used for remote-controlling the clinical specimen processing device; and image supply means for supplying a picked-up image obtained by the image pickup device to the control apparatus through a communication network, wherein the control apparatus displays the picked-up image supplied by the image supply means.

The third aspect of the present invention relates to a status informing device, which informs the status of a clinical specimen processing device for processing a clinical specimen, comprising: status information acquiring means for acquiring status information relating to the state of the clinical specimen processing device; status information transmitting means for transmitting the status information acquired by the status information acquiring means; image acquiring means for acquiring a picked-up image of the clinical specimen processing device; and image transmitting means for transmitting the picked-up image acquired by the image acquiring means.

The fourth aspect of the present invention relates to a clinical specimen processing device, which processes a clinical specimen, comprising: a mechanism unit used for processing the clinical specimen; an image pickup unit that picks up an image of the mechanism unit; and image supply means for supplying the picked-up image by the image pickup unit to a control apparatus to be used for remote-controlling the clinical specimen processing device through a communication network.

The fifth aspect of the present invention relates to a control apparatus, which is used for remote-controlling a clinical specimen processing device for processing a clinical specimen, comprising: status information receiving means for receiving status information concerning the state of the clinical specimen processing device; image receiving means for receiving a picked-up image of the clinical specimen processing device; and display means for displaying the picked-up image received by the image receiving means.

DETAILED DESCRIPTION

The preferred embodiments of the present invention are described hereinafter with reference to the drawings.

Figure 1:
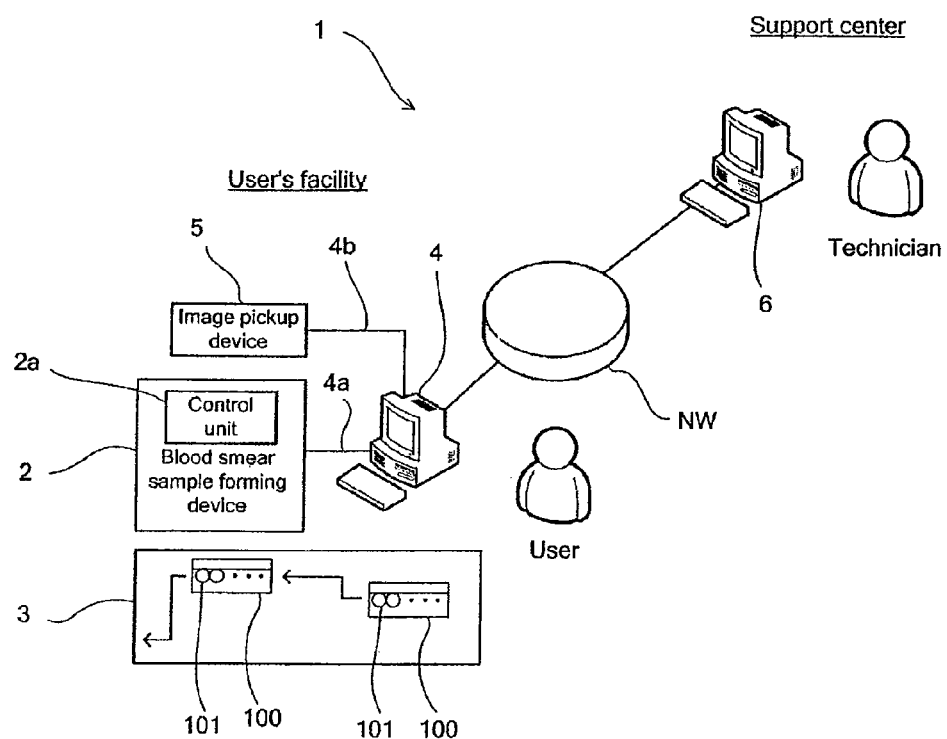
FIG. 1 is a schematic block diagram that shows a configuration of a remote control system in accordance with one embodiment of the present invention.

FIG. 1 is a schematic block diagram that shows a configuration of a remote control system in accordance with one embodiment of the present invention. As shown in FIG. 1, a remote control system 1 in accordance with the present embodiment is mainly constituted by a blood smear sample forming device 2, a transporting device 3, a computer 4 that functions as a status informing device in accordance with the present invention, an image pickup device 5 and a computer 6 that functions as a control apparatus in accordance with the present invention. The blood smear sample forming device 2, the transporting device 3, the computer 4 and the image pickup device 5 are installed, for example, in a facility of a medical organization such as a hospital or a pathology inspection facility, and the computer 6 is installed in a facility of a support center that carries out supporting processes on maintenance and controlling operations of the blood smear sample forming device 2. The blood smear sample forming device 2 and the computer 4 are connected to each other through an electric signal cable 4a so as to allow data communication with each other, and the computer 4 and the image pickup device 5 are connected to each other through an electric signal cable 4b so as to transmit an image signal of the image pickup device 5 to the computer 4. Moreover, the computer 4 and the computer 6 are connected to each other through a communication network NW, such as a dedicated line using a telephone line, a wired network, a wireless network, LAN, the Internet, or a combination of above, so as to allow data communication with each other.

Figure 2:
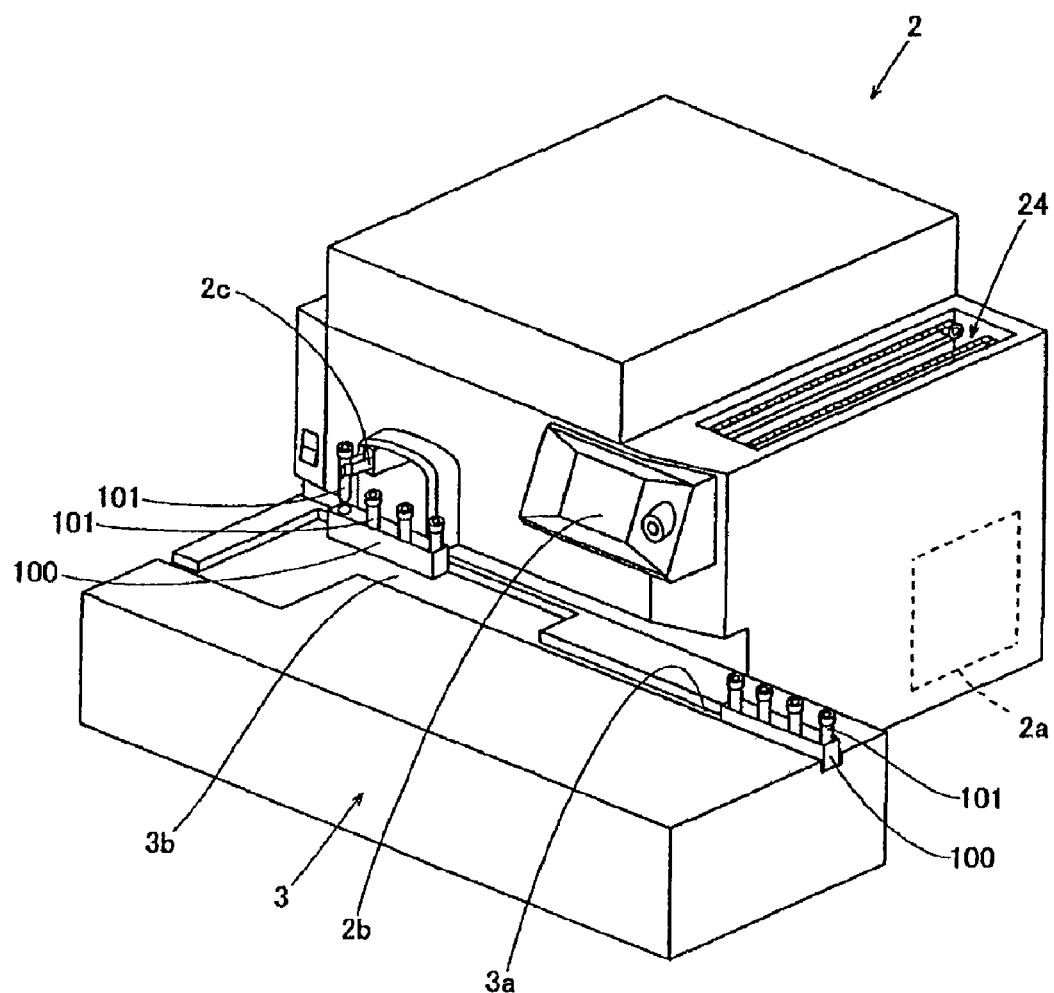
FIG. 2 is a perspective view that shows a configuration of a blood smear sample forming device in accordance with the embodiment of the present invention.

FIG. 2 is a perspective view that shows a configuration of a blood smear sample forming device in accordance with the embodiment of the present invention. The blood smear sample forming device 2 is installed so as to produce a smear sample for a blood specimen. The blood smear sample forming device 2 includes a control unit 2a, and is connected to the computer 4. In the present embodiment, the control unit 2a of the blood smear sample forming device 2 is constituted by a CPU, a ROM, a RAM or the like. The control unit 2a has functions for operation-controlling the blood smear sample forming device 2, for determining whether or not the blood smear sample forming device 2 is in an abnormal state, for determining whether or not the blood smear sample forming device 2 is in a warning state having a higher possibility of malfunction in the future in comparison with a normal state, and for transmitting information that the blood smear sample forming device 2 is in an abnormal state or in a warning state (abnormal information and warning information) to the computer 4. Moreover, the transporting device 3, which is placed in front of the blood smear sample forming device 2, is provided with a carry-in unit 3a and a take-out unit 3b. The transporting device 3 is used for automatically transporting a specimen lack 100 housing test tubes 101 in which blood is stored to the blood smear sample forming device 2.

Figure 3:
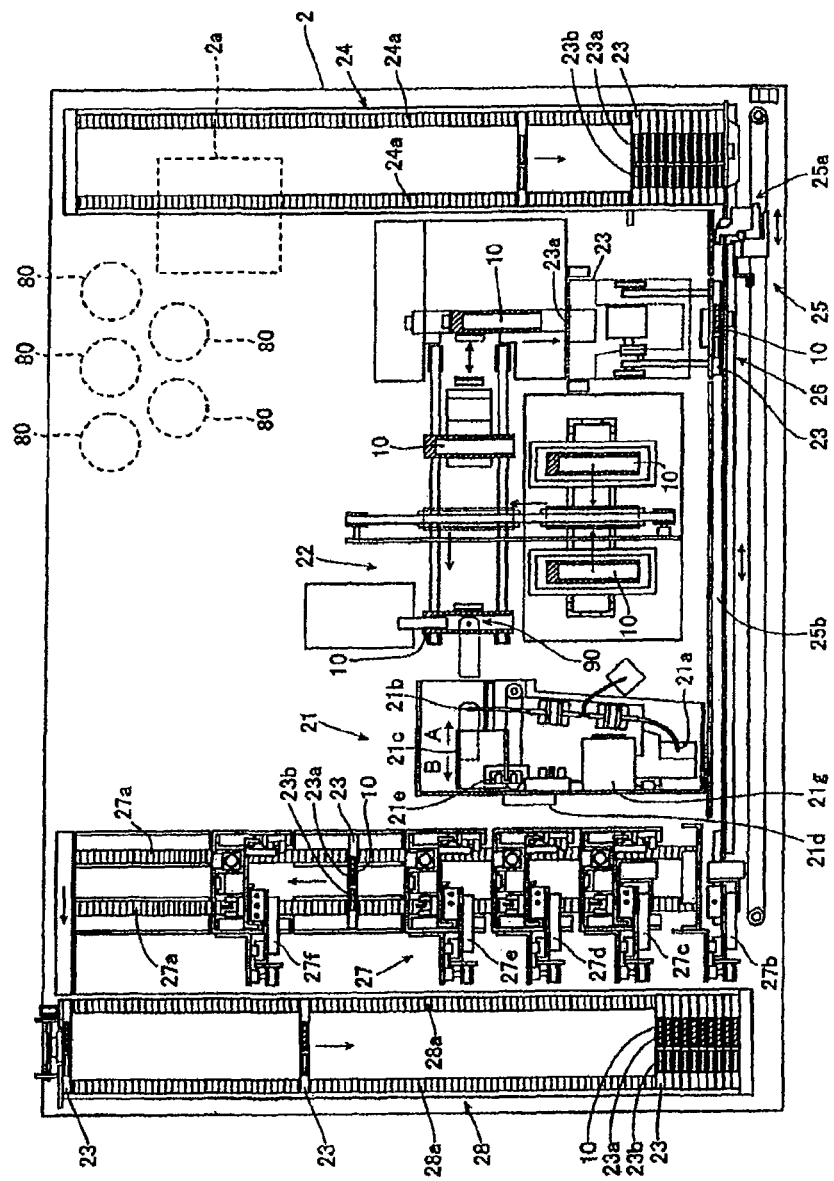
FIG. 3 is a plan view that shows an inner structure of the blood smear sample forming device in accordance with the embodiment of the present invention.
Figure 4:
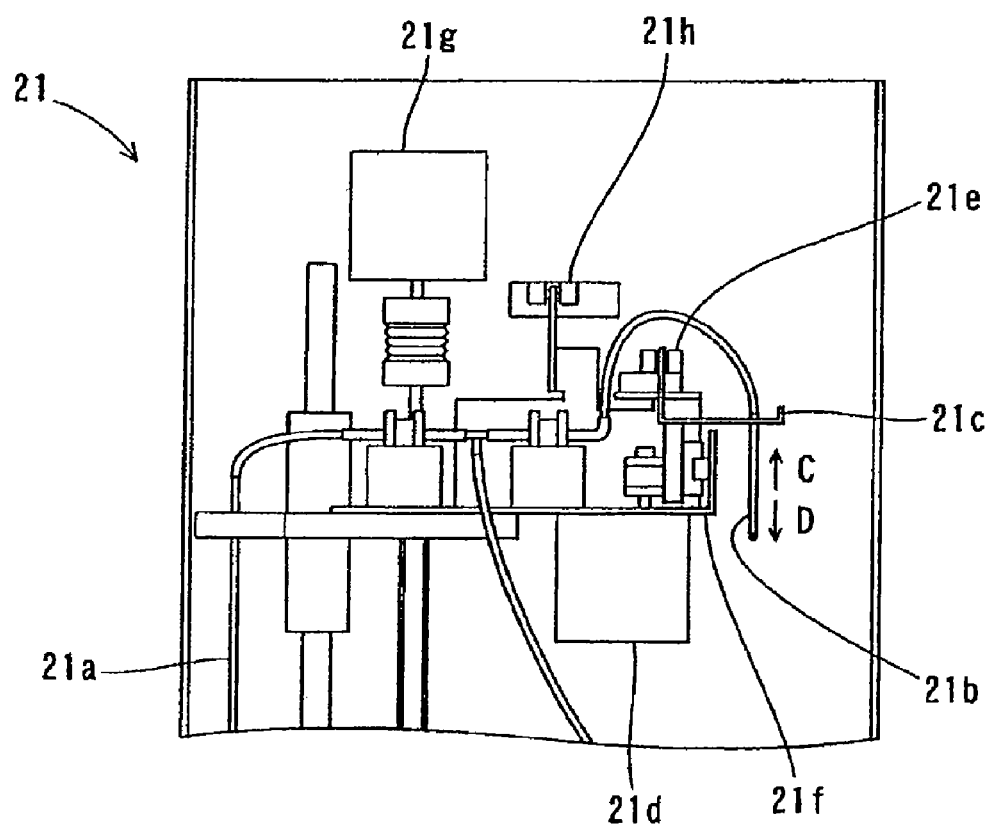
FIG. 4 is a plan view that shows a configuration of a suction dispensation mechanism unit of the blood smear sample forming device in accordance with the embodiment of the present invention.
Figure 5:
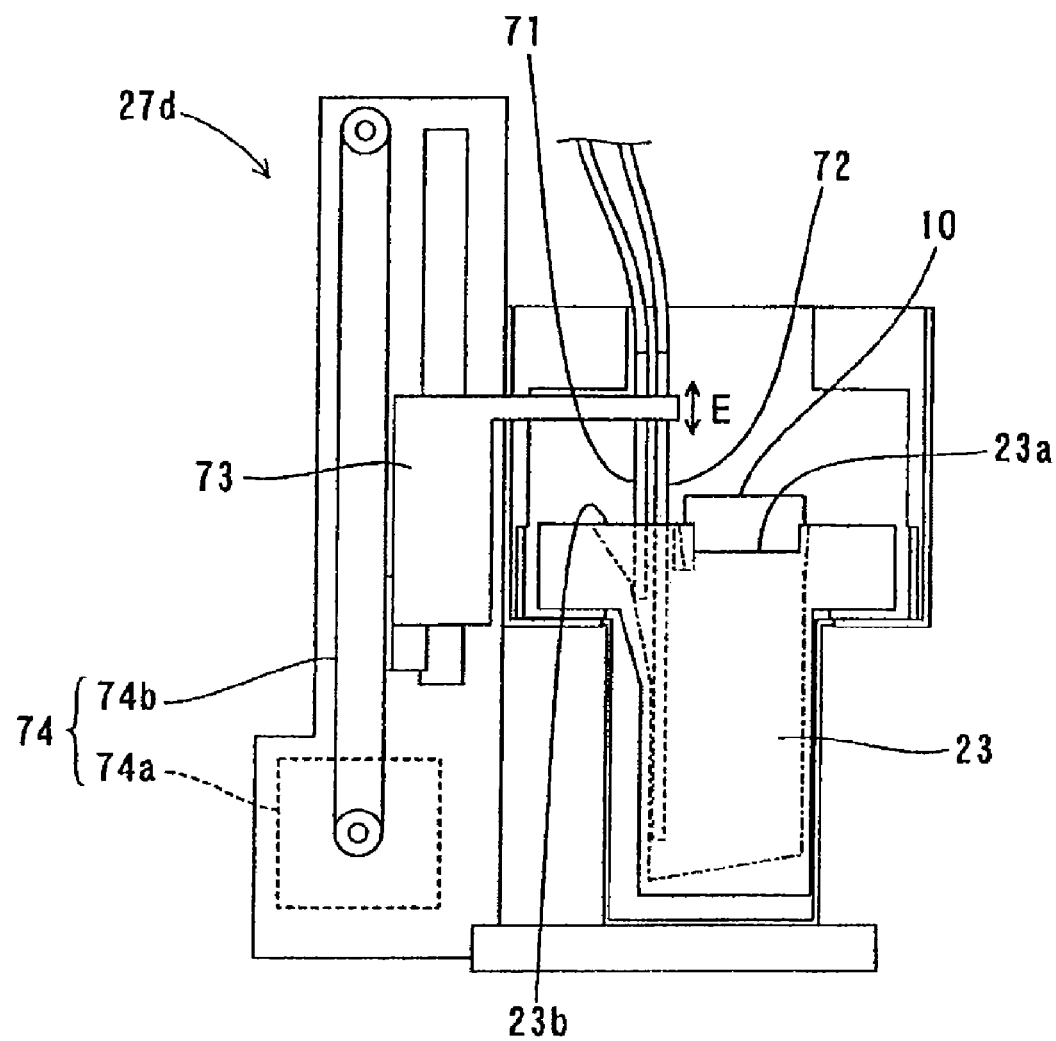
FIG. 5 is a plan view that shows a configuration of a third suction discharging unit of a dyeing unit of the blood smear sample forming device in accordance with the embodiment of the present invention.
Figure 6:
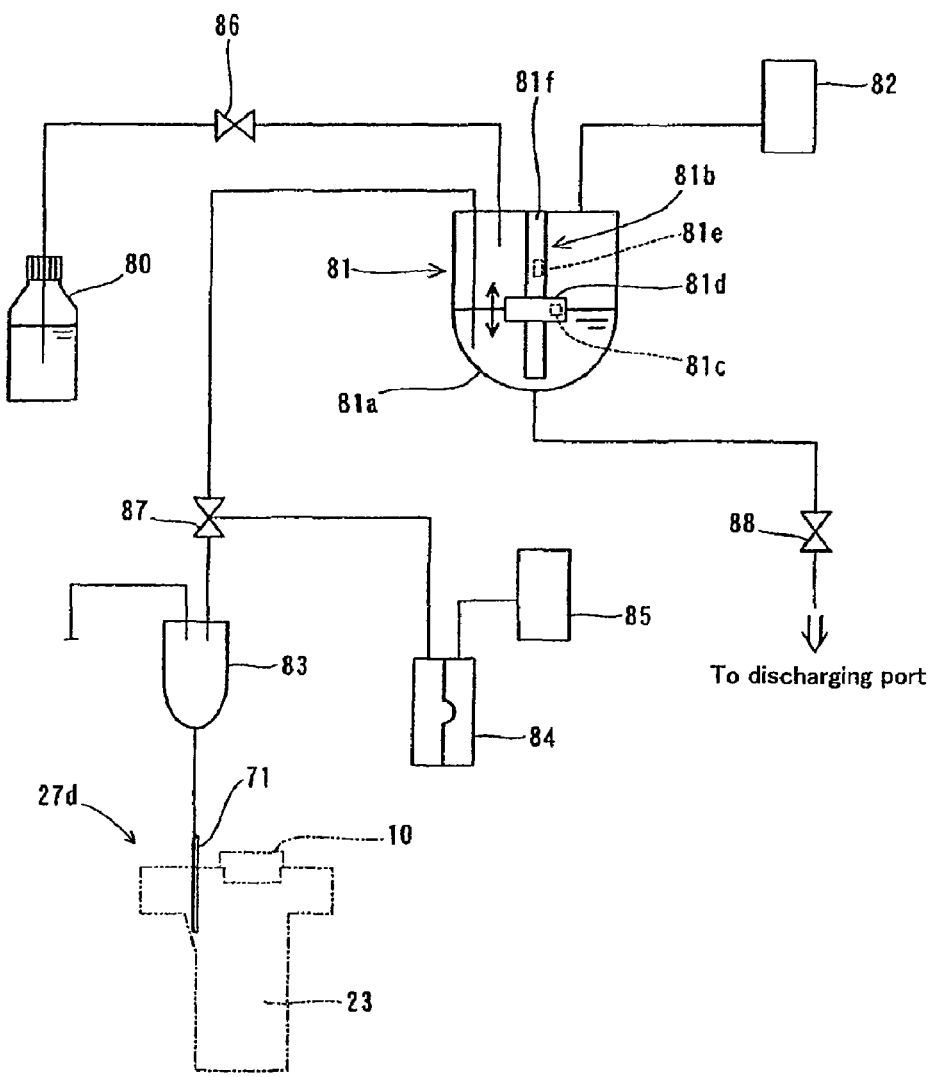
FIG. 6 is a fluid circuit diagram that shows a supply path of a dyeing solution to be supplied to the third suction discharging unit of a dyeing unit shown in FIG. 5.

FIGS. 3 to 5 are drawings that explain the structure of the blood smear sample forming device, and FIG. 6 is a fluid circuit diagram that shows a supply path of a dyeing solution to be supplied to a third suction discharge unit of a dyeing unit of the blood smear sample forming device. Referring to FIGS. 2 to 6, the following description explains the entire configuration of the blood smear sample forming device 2 and the transporting device 3. As shown in FIG. 2, in addition to the control unit 2a, the blood smear sample forming device 2 is provided with a display operation unit 2b made of a touch panel and a hand member 2c used for transporting a test tube 101 in which blood is stored from the transporting device 3 side to the blood smear sample forming device 2 side. As shown in FIG. 3, the blood smear sample forming device 2 is also provided with a suction dispensation mechanism unit 21, a smearing unit 22, a resin-made cassette 23, a cassette housing unit 24, a cassette transporting unit 25, a slide glass plate insertion unit 26, a dyeing unit 27, and a storing unit 28. Moreover, as shown in FIG. 3, a plurality of containers 80, which house a dyeing solution to be used in the dyeing unit 27 and washing water, are placed below the blood smear sample forming device 2.

The suction dispensation mechanism unit 21 sucks blood from the test tube 101 transported to the blood smear sample forming device 2 side by the hand member 2c (see FIG. 2), and drops the drawn blood onto a slide glass plate 10. As shown in FIG. 4, the suction dispensation mechanism unit 21 includes: a piercer (suction syringe) 21a used for drawing blood from the test tube 101 (see FIG. 2), a dispensation pipette 21b for delivering drawn blood onto slide glass plates 10, a supporting member 21c that supports the dispensation pipette 21b, a forward/rearward driving motor 21d that shifts the supporting member 21c forward (direction of arrow A in FIG. 3) as well as rearward (direction of arrow B in FIG. 3), a sensor 21e used for detecting the origin position in the horizontal direction of the dispensation pipette 21b by detecting a predetermined portion of the supporting member 21c, a supporting member 21f that supports the supporting member 21c and the forward/rearward driving motor 21d, an upward/downward driving motor 21g that shifts the supporting member 21f upward (direction of arrow C in FIG. 4) as well as downward (direction of arrow D in FIG. 4) and a sensor 21h used for detecting the origin position in the vertical direction of the dispensation pipette 21b by detecting a predetermined portion of the supporting member 21f. Here, with respect to the forward/rearward driving motor 21d and the upward/downward driving motor 21g, stepping motors that operate upon receipt of a pulse signal are used.

As shown in FIG. 3, the smearing unit 22 supplies a slide glass plate 10 to a dispensing and smearing position 90, and smears blood dropped onto the slide glass plate 10 to be dried thereon, and also carries out a printing process on the slide glass plate 10. Here, the cassette 23, made of resin, is designed to house the slide glass plate 10 that has been subjected to the smearing process and a liquid (dyeing solution) to be used in the dyeing process. As shown in FIG. 5 this cassette 23 includes a slide glass plate housing slot 23a and a dyeing solution suction dispensing hole 23b. The slide glass plate housing slot 23a and the dyeing solution suction dispensing hole 23b are allowed to communicate with each other inside.

As shown in FIG. 3, a cassette housing unit 24 is used for carrying the cassette 23 to a cassette transporting unit 25, and includes a feeding belt 24a. Moreover, the cassette transporting unit 25 transports the cassette 23 brought from the cassette housing unit 24 to a slide glass plate insertion unit 26 and a dyeing unit 27. As shown in FIG. 3, the cassette transporting unit 25 includes a cassette transporting member 25a capable of shifting in horizontal directions and a transport path 25b used for transporting the cassette 23 supplied from the cassette housing unit 24. Here, the slide glass plate insertion unit 26, shown in FIG. 3, is designed to place the slide glass plate 10 that has been subjected to the smearing process and a printing process into the slide glass plate housing slot 23a of the cassette 23.

The dyeing unit 27 shown in FIG. 3 is designed to dye the slide glass plate 10 with the smearing by supplying a dyeing solution to the dyeing solution suction dispensing hole 23b of the cassette 23 transported by the cassette transporting member 25a. The dyeing unit 27 includes a conveyor belt 27a for transporting the cassette 23 and first to fifth suction discharging units 27b to 27f that are used for supplying and discharging the dyeing solution to and from the cassette 23.

By exemplifying the third suction discharging unit 27d among the first to fifth suction discharging units 27b to 27f by reference to FIGS. 5 and 6, the following description will discuss the structure and the fluid paths of the dyeing solution used in the third suction discharging unit 27d. As shown in FIG. 5, the third suction discharging unit 27d is provided with a supply pipette 71 and a discharge pipette 72 which respectively supplies and discharges the dyeing solution to and from the cassette 23, a pipette supporting member 73 that supports the supply pipette 71 and the discharge pipette 72, and a driving mechanism unit 74 including a motor 74a and a driving belt 74b used for shifting the pipette supporting member 73 upward and downward (directions indicated by E in FIG. 5). The third suction discharging unit 27d allows the driving mechanism unit 74 to shift the supply pipette 71 and the discharge pipette 72 downward with respect to the cassette 23 so that the dyeing solution is supplied and discharged.

As shown in FIG. 6, the fluid paths of the dyeing solution supplied from the supply pipette 71 of the third suction discharging unit 27d include a container 80 that houses the dyeing solution, a chamber 81 that temporarily stores the dyeing solution, an atmospheric pressure regulator 82 that carries out compressing and decompressing operations on the chamber 81, a mixing chamber 83 that is used for mixing the dyeing solution and a dilution for diluting the dyeing solution, a diaphragm pump 84 that transfers the dyeing solution between the chamber 81 and the mixing chamber 83, and an atmospheric pressure regulator 85 that carries out compressing and decompressing operations on the diaphragm pump 84. The chamber 81 is connected to the container 80, the atmospheric pressure regulator 82, the mixing chamber 83 and the discharging port through pipes. The mixing chamber 83 is connected to the supply pipette 71 of the third suction discharging unit 27d of the dyeing unit 27 through a pipe. Moreover, valves 86, 87 and 88 are respectively installed between the container 80 and the chamber 81, between the chamber 81 and the mixing chamber 83 and between the chamber 81 and the discharging port. The diaphragm pump 84 is connected to the valve 87 through a pipe. Moreover, a pipe used for supplying a diluent for diluting the dyeing solution is connected to the mixing chamber 83.

As shown in FIG. 6, the chamber 81 is provided with a reservoir unit 81a that houses the dyeing solution and a float switch 81b placed inside the reservoir unit 81a. The float switch 81b, which is made from materials capable of floating on the dyeing solution, is constituted by a float member 81d in which a magnet 81c is embedded and a supporting rod 81f that supports the float member 81d in a manner so as to shift upward and downward and has a built-in lead switch 81e of a magnetic detection type. Moreover, the lead switch 81e is embedded in a predetermined position of a supporting rod 81f that is capable of detecting a magnetic filed of the magnet 81c of the float member 81d when the dyeing solution inside the reservoir unit 81a has reached a predetermined amount. With respect to the float switch 81b, when the float member 81d approaches a predetermined position, the lead switch 81e of the supporting rod 81f detects the magnetic field of the magnet 81c inside the float member 81d to be turned on, and when the float member 81d departs from the predetermined position, the lead switch 81e of the supporting rod 81f no longer detects the magnetic field of the magnet 81c inside the float member 81d to be turned off.

Moreover, the storing unit 28, shown in FIG. 3, is used for storing the cassette 23 that houses the slide glass plate 10 that has been dyed in the dyeing unit 27. The storing unit 28 is provided with a conveyor belt 28a used for transporting the cassette 23.

Figure 7:
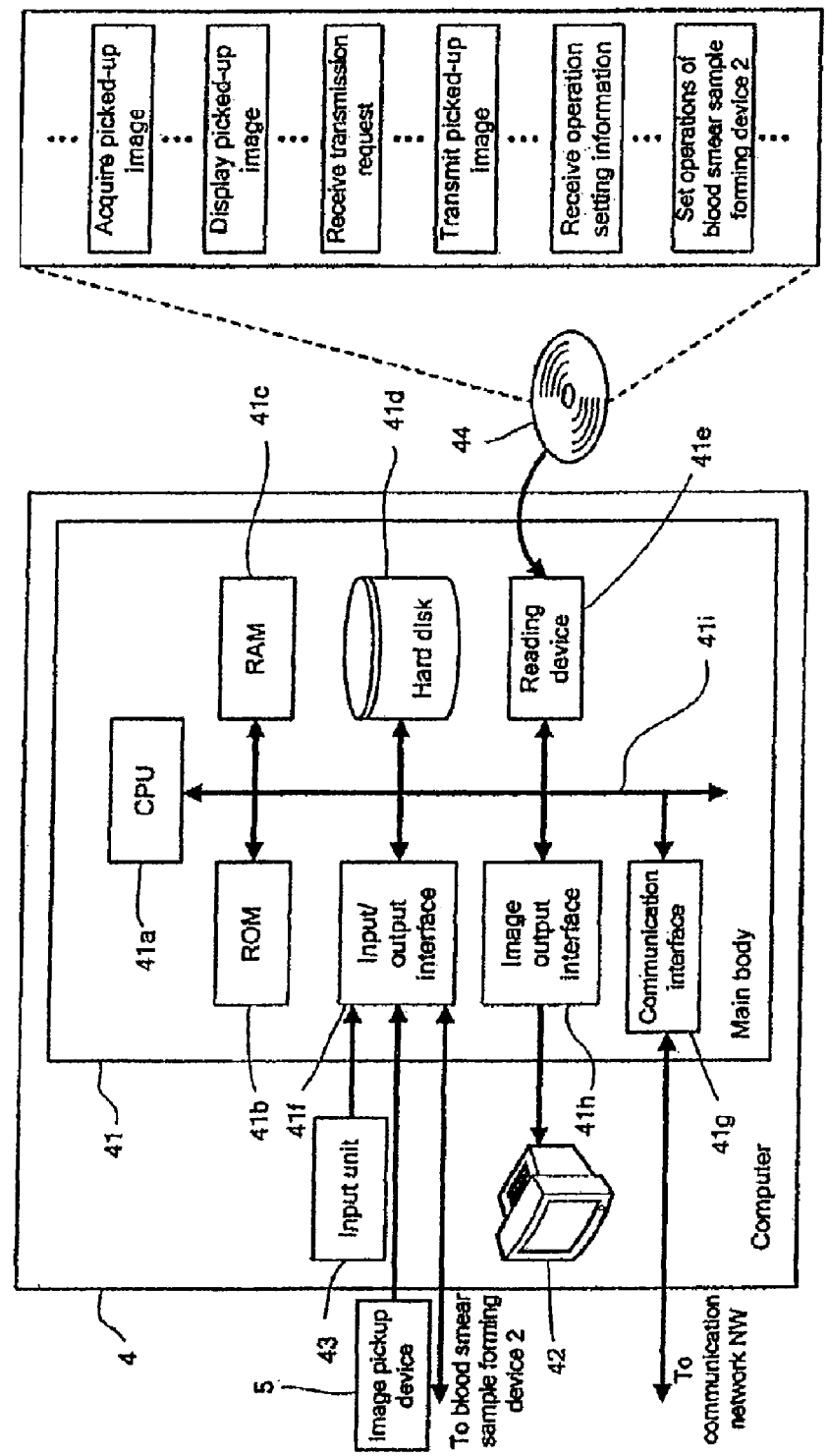
FIG. 7 is a block diagram that shows a configuration of a status informing device in accordance with the embodiment of the present invention.

The following description will discuss the configuration of the computer 4. FIG. 7 is a block diagram that shows the configuration of the computer 4 in accordance with the embodiment of the present invention. The computer 4 is mainly constituted by a main body 41, an image display unit 42 and an input unit 43. The main body 41 is mainly constituted by a CPU 41a, a ROM 41b, a RAM 41c, a hard disk 41d, a reading device 41e, an input/output interface 41f, a communication interface 41g and an image output interface 41h, and the CPU 41a, the ROM 41b, the RAM 41c, the hard disk 41d, the reading device 41e, the input/output interface 41f, the communication interface 41g and the image output interface 41h are connected to one another through a bus 41i.

The CPU 41a can execute computer programs stored in the ROM 41b and computer programs loaded to the RAM 41c. Thus, the CPU 41a executes a computer program which will be described later so that the computer 4 functions as a status informing device in accordance with the present invention.

The ROM 41b is constituted by a mask ROM, a PROM, an EPROM, an EEPROM and the like so that computer programs to be executed by the CPU 41a and data and the like to be used in combination are recorded therein.

The RAM 41c is constituted by an SRAM, a DRAM or the like. The RAM 41c is used for reading computer programs recorded in the ROM 41b and the hard disk 41d. When these computer programs are executed, the RAM 41c is utilized as the working area of the CPU 41a.

The hard disk 41d has various computer programs to be executed by the CPU 41a, such as an operating system and application programs, as well as data used for executing the computer programs installed therein.

The reading device 41e is constituted by a flexible disk drive, a CD-ROM drive, a DVD-ROM drive or the like, and can read computer programs or data recorded in a portable-type recording medium 44. Here, a computer program, used for allowing the computer to function as the status informing device, is stored in the portable-type recording medium 44; thus, the computer 4 may read the computer program from the portable-type recording medium 44 so that the computer program is installed in the hard disk 41d.

Here, the computer program is not only supplied by the portable-type recording medium 44, but also supplied through an electric communication line (irrespective of cable or radio) from an external device communicatably connected to the computer 4 by the line. For example, the computer program in accordance with the present invention may be stored in a hard disk of a server computer on the Internet, and by allowing the computer 4 to access this server computer, the computer program may be downloaded and installed in the hard disk 41d.

The input/output interface 41f is constituted by, for example, a serial interface such as USB, IEEE1394 and RS-232C, a parallel interface such as SCSI, IDE and IEEE 1284, and an analog interface made of a D/A converter, an A/D converter and the like. An input unit 43, that is, a keyboard and a mouse, is connected to the input/output interface 41f, and when the user (for example, an inspector or an inspection doctor) operates the input unit 43 so that data can be inputted to the computer 4.

Moreover, the image pickup device 5 described above is connected to the input/output interface 41f through, for example, USB so that an image signal of the image pickup device 5 can be taken through the interface. The image pickup device 5 is formed by a CCD camera, a CMOS camera or the like, and an image of a subject is picked up at a predetermined frame rate so that an image signal (dynamic image signal) is outputted. Here, the image pickup device 5 is preferably prepared as a color video camera, or a monochrome video camera may be used.

The blood smear sample forming device 2 described above is connected to the input/output interface 41f through, for example, USB so that warning information and error information, which will be described later, are received from the blood smear sample forming device 2, and operation settings can be carried out on the blood smear sample forming device 2.

The communication interface 41g is prepared as, for example, an Ethernet (registered trademark) interface, and the computer 4 can transmit and receive data to and from a computer 6 connected to the communication network NW by using a predetermined communication protocol through the communication interface 41g.

The image output interface 41h is connected to the image display unit 42 made of an LCD, a CRT or the like so that an image signal corresponding to image data given from the CPU 41a is outputted to the image display unit 42. The image display unit 42 displays an image (screen image) in accordance with the inputted image signal.

Figure 8:
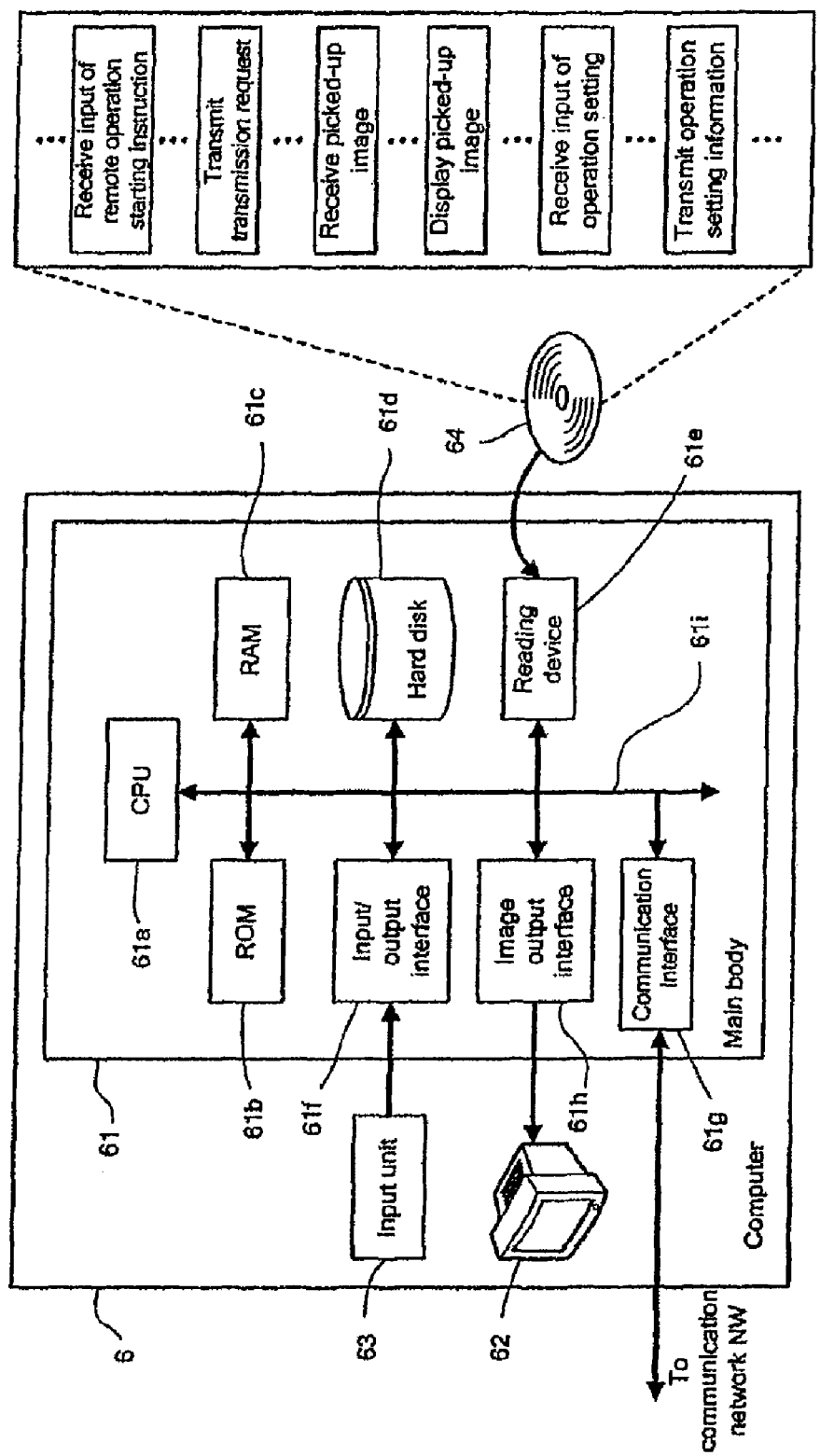
FIG. 8 is a block diagram that shows a configuration of a control apparatus in accordance with the embodiment of the present invention.

Next, the following description will discuss the configuration of the computer 6. FIG. 8 is a block diagram that shows the configuration of the computer 6 in accordance with the embodiment of the present invention. The computer 6 is mainly constituted by a main body 61, an image display unit 62 and an input unit 63. The main body 61 is mainly constituted by a CPU 61a, a ROM 61b, a RAM 61c, a hard disk 61d, a reading device 61e, an input/output interface 61f, a communication interface 61g and an image output interface 61h, and the CPU 61a, the ROM 61b, the RAM 61c, the hard disk 61d, the reading device 61e, the input/output interface 61f, the communication interface 61g and the image output interface 61h are connected to one another through a bus 61i.

The CPU 61a can execute computer programs stored in the ROM 61b and computer programs loaded to the RAM 61c. Thus, the CPU 61a executes a computer program which will be described later so that the computer 6 functions as a control apparatus in accordance with the present invention.

The ROM 61b is constituted by a mask ROM, a PROM, an EPROM, an EEPROM and the like so that computer programs to be executed by the CPU 61a and data and the like to be used in combination are recorded therein.

The RAM 61c is constituted by an SRAM, a DRAM or the like. The RAM 61c is used for reading computer programs recorded in the ROM 61b and the hard disk 61d. When these computer programs are executed, the RAM 61c is utilized as the working area of the CPU 61a.

The hard disk 61d has various computer programs to be executed by the CPU 61a, such as an operating system and application programs, as well as data used for executing the computer programs installed therein. Moreover, a receiving server program for electronic mails is installed in the hard disk 61d, and a mail box (not shown) for electronic mails in association with an electronic mail address used for informing the status of a clinical specimen processing device. When an electronic mail is transmitted to the corresponding electronic mail address from an external computer 4, the electronic mail receiving server program, executed by the CPU 61a, receives the electronic mail and stores the mail in the mail box.

The reading device 61e is constituted by a flexible disk drive, a CD-ROM drive, a DVD-ROM drive or the like, and can read computer programs or data recorded in a portable-type recording medium 64. Here, a computer program, used for allowing the computer to function as the control apparatus, is stored in the portable-type recording medium 64; thus, the computer 6 may read the computer program from the portable-type recording medium 64 so that the computer program is installed in the hard disk 61d.

Here, the computer program can be not only supplied by the portable-type recording medium 64, but also supplied through an electric communication line (irrespective of cable or radio) from an external device communicatably connected to the computer 6 by the line. For example, the computer program in accordance with the present invention may be stored in a hard disk of a server computer on the Internet, and by allowing the computer 6 to access this server computer, the computer program may be downloaded and installed in the hard disk 61d.

The input/output interface 61f is constituted by, for example, a serial interface such as USB, IEEE1394 and RS-232C, a parallel interface such as SCSI, IDE and IEEE 1284, and an analog interface made of a D/A converter, an A/D converter and the like. An input unit 63, that is, a keyboard and a mouse, is connected to the input/output interface 61f, and when a technician in the support center operates the input unit 63 so that data can be inputted to the computer 6.

The communication interface 61g is prepared as, for example, an Ethernet (registered trademark) interface, and the computer 6 can transmit and receive data between a computer 4 connected to the communication network NW by using a predetermined communication protocol through the communication interface 61g.

The image output interface 61h is connected to the image display unit 62 made of an LCD, a CRT or the like so that an image signal corresponding to image data given from the CPU 61a is outputted to the image display unit 62. The image display unit 62 displays an image (screen image) in accordance with the inputted image signal.

The following description will discuss operations of the remote control system 1 in accordance with the present embodiment. First, carte information of a supplier of a specimen (patient) is inputted to a host computer, not shown. Then, the blood smear sample forming device 2, shown in FIGS. 1 and 2 samples the blood specimen from a test tube 101 placed on a specimen rack 100 to be transported by the transporting device 3, and forms a blood smear sample, in accordance with the information of the host computer.

Upon forming the blood smear sample by using the blood smear sample forming device 2, first, as shown in FIG. 2, the specimen rack 100 on which the test tube 101 containing a blood specimen is mounted is set at the carry-in unit 3a of the transporting device 3, in a suction dispensing operation. Then, a start switch for an automatic suction operation displayed on the display operation unit 2b is pressed down. Thus, the specimen rack 100 is transported to the take-out unit 3b of the transporting device 3. The hand member 2c of the blood smear sample forming device 2 raises the test tube 101 of the specimen rack 100, and after stirring the specimen, it places the test tube 101 in the suction dispensation mechanism unit 21 shown in FIG. 3. Then, the blood inside the test tube 101 is sucked by the piercer 21a. Next, after the dispensation pipette 21b has been shifted forward (direction indicated by arrow A in FIG. 3) and downward (direction indicated by arrow D in FIG. 4) to be placed at the dispensing and smearing position 90 shown in FIG. 3, the blood is dropped (dispensed) onto a slide glass plate 10 from the dispensation pipette 21b. After this dispensing operation, the dispensation pipette 21b is shifted upward (direction indicated by arrow C in FIG. 4) and rearward (direction indicated by arrow B in FIG. 3) to be placed at the origin position. In the case when the dispensation pipette 21b is shifted upward, the upward/downward driving motor 21g is driven with the dispensation pipette 21b located at the lower end position after the dispensing operation. Thus, the supporting member 21f supporting the dispensation pipette 21b is shifted in a direction indicated by arrow C in FIG. 4. By detecting the supporting member 21f by the sensor 21h, the driving operation of the upward/downward driving motor 21g is stopped. The raising operation of the dispensation pipette 21b is controlled by the control unit 2a of the blood smear sample forming device 2.

Figure 9:
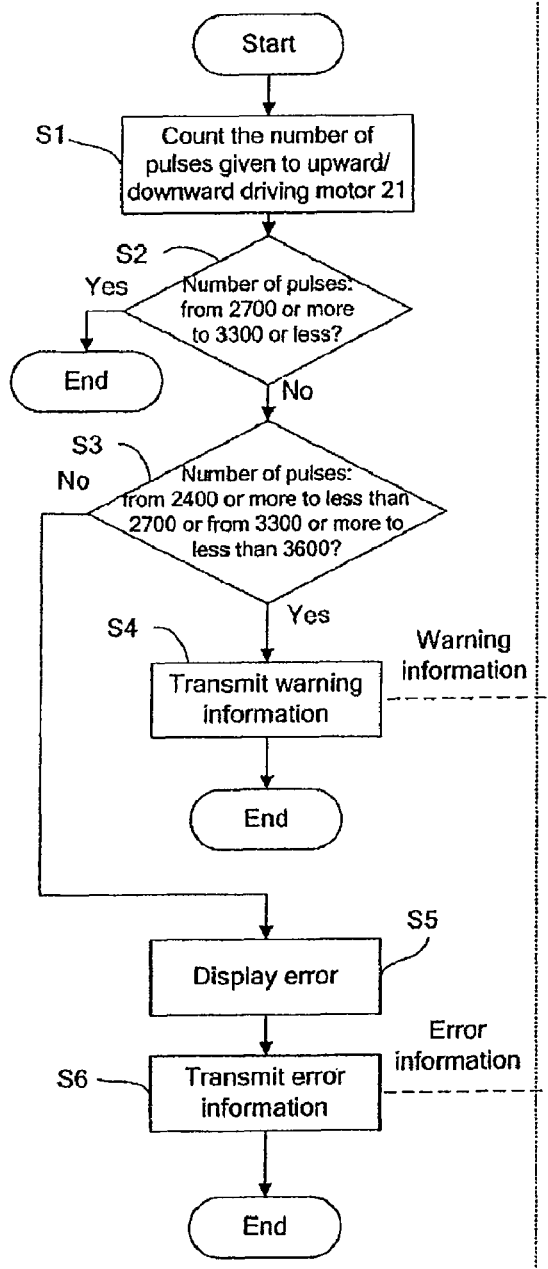
FIG. 9 is a flow chart that explains a sequence of status informing processes during a raising operation of an dispensation pipette in the remote control system in accordance with the embodiment of the present invention.
Figure 9:
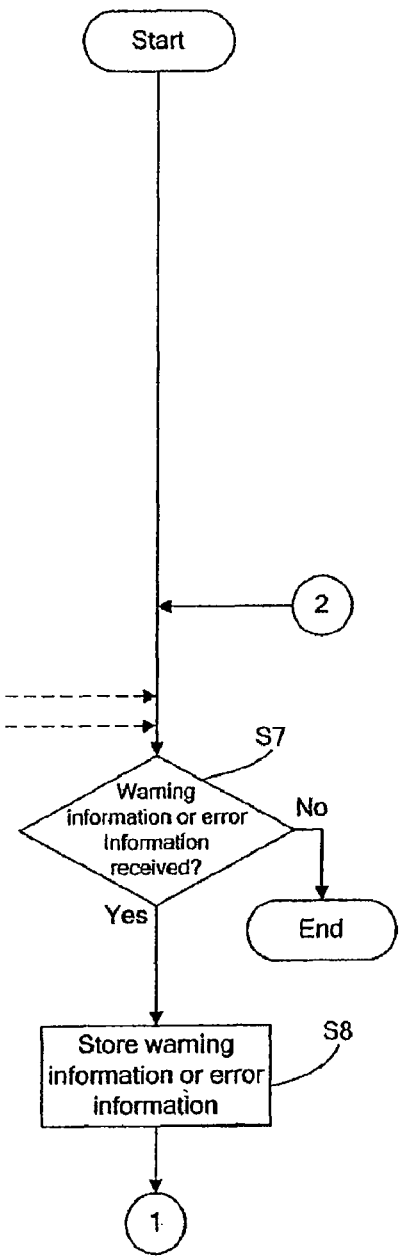
Figure 10:
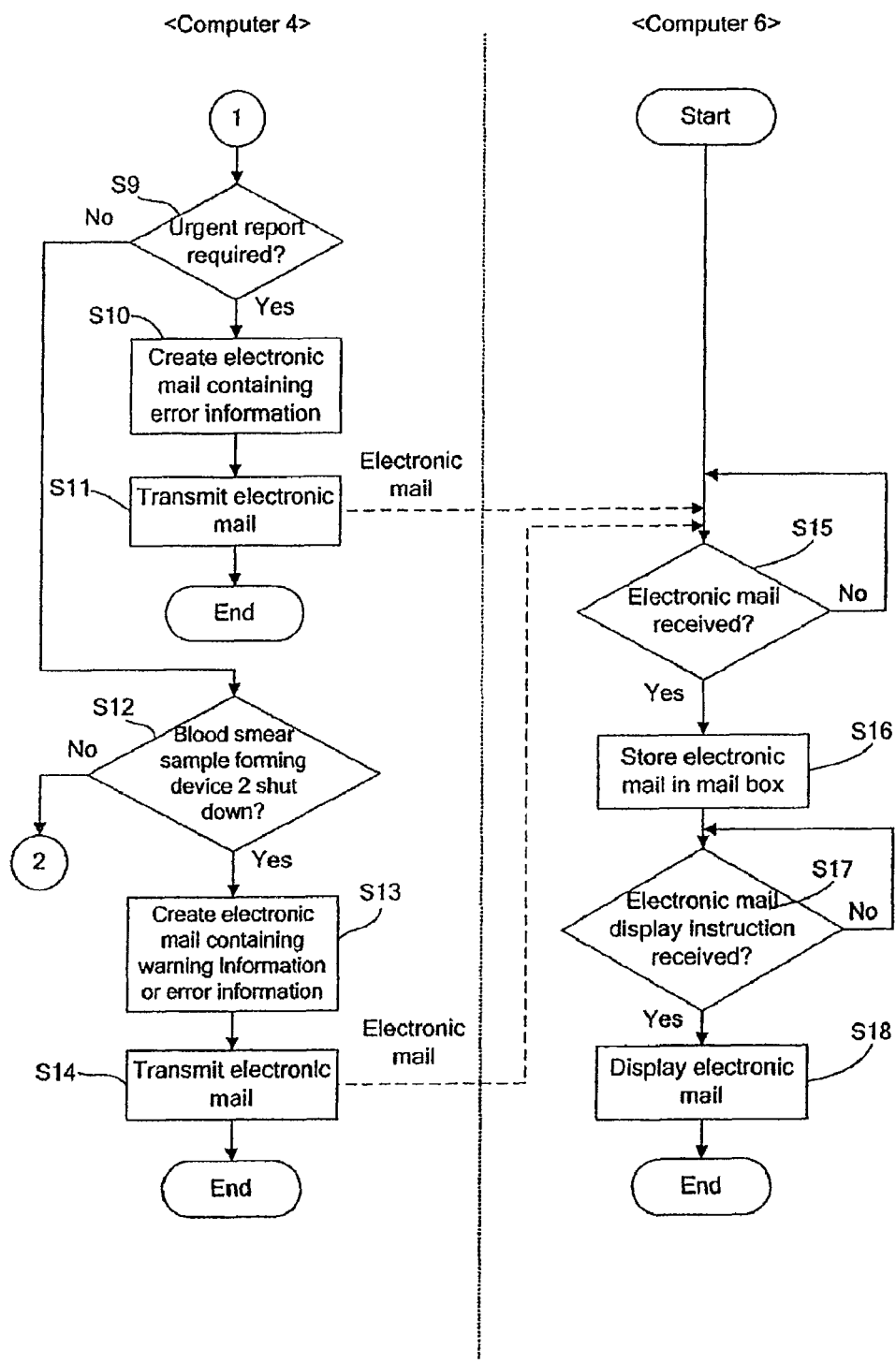
FIG. 10 is a flow chart that explains a sequence of status informing processes during a raising operation of an dispensation pipette in the remote control system in accordance with the embodiment of the present invention.

The following description will discuss a status informing process during the raising operation of the dispensation pipette 21b in accordance with the present embodiment. FIGS. 9 and 10 are flow charts that explain a sequence of the status informing process during the raising operation of the dispensation pipette of the control system in accordance with the embodiment of the present invention. First, the control unit 2a of the blood smear sample forming device 2 drives the upward/downward driving motor 21g so as to shift the dispensation pipette 21b upward (direction indicated by arrow C in FIG. 4), and at this time, the number of pulses of a pulse signal given to the upward/downward driving motor 21 is counted (step S1). Upon completion of the raising operation of the dispensation pipette 21b, the control unit 2a determines whether or not the number of pulses that have been given to the upward/downward driving motor 21g from the start to the completion of the raising operation of the dispensation pipette 21b is located within a range from 2700 or more to 3300 or less (step S2). At step S2, when it is determined that the number of pulses that have been given to the upward/downward driving motor 21g from the start to the completion of the raising operation of the dispensation pipette 21b is located within a range from 2700 or more to 3300 or less (Yes at step S2), the raising operation of the dispensation pipette 21b is determined to be in a normal state so that the control unit 2a continues the rest of the sequence of the blood smear sample forming processes, and the processes are completed. At step S2, when it is determined that the number of pulses that have been given to the upward/downward driving motor 21g from the start to the completion of the raising operation of the dispensation pipette 21b is not located within a range from 2700 or more to 3300 or less (No at step S2), the control unit 2a determines whether or not the number of pulses that have been given to the upward/downward driving motor 21g from the start to the completion of the raising operation of the dispensation pipette 21b is located within a range from 2400 or more to less than 2700 or within a range from 3300 or more to less than 3600 (step S3). At step S3, when it is determined that the number of pulses that have been given to the upward/downward driving motor 21g from the start to the completion of the raising operation of the dispensation pipette 21b is located within a range from 2400 or more to less than 2700 or within a range from 3300 or more to less than 3600 (Yes at step S3), the driving mechanism of the dispensation pipette 21b is determined to be in a state having a high possibility of malfunction in the future (warning state). Therefore, in this case, the control unit 2a transmits warning information indicating that the driving mechanism of the dispensation pipette 21b is in a state having a high possibility of malfunction in the future to the computer 4 (step S4), and then continues the rest of the sequence of blood smear sample forming processes so that the processes are completed.

At step S3, when it is determined that the number of pulses that have been given to the upward/downward driving motor 21g from the start to the completion of the raising operation of the dispensation pipette 21b is located neither within a range from 2400 or more to less than 2700, nor within a range from 3300 or more to less than 3600 (No at step S3), the driving mechanism of the dispensation pipette 21b is determined to be in an abnormal (error) state. Therefore, in this case, the control unit 2a of the blood smear sample forming device 2 displays an error message indicating the abnormal state of the driving mechanism of the dispensation pipette 21b (step S5) on the display operation unit 2b of the blood smear sample forming device 2, and transmits error information indicating the abnormal state to the computer 4 (step S6). When warning information or error information is transmitted from the blood smear sample forming device 2, the CPU 41a of the computer 4 receives the information through the communication interface 41g (Yes in step S7), and stores the received warning information or error information in the RAM 41c (step S8).

Next, when the data received at step S7 corresponds to error information, the CPU 41a determines whether or not the error information is required to be urgently informed (step S9). In this process, for example, among pieces of error information, those pieces of error information required to be urgently informed are preliminarily determined, and it is determined whether or not the corresponding data match any of the pieces of error information. At step S9, when the error information is determined to be urgently informed (Yes in step S9), the CPU 41a of the computer 4 forms an electronic mail that contains the error information stored in the RAM 41c of the computer 4 in the body portion or the added file and is directed to the electronic mail address used for informing the status of a clinical specimen processing device (step S10), and transmits the electronic mail immediately (step S11), thereby completing the processes.

In contrast, at step S9, in the case when it is determined that the error information is not required to be urgently informed (No in step S9), at the time of shutting down the blood smear sample forming device 2 (Yes in step S12), the CPU 41a of the computer 4 forms an electronic mail that contains the error information or warning information stored in the RAM 41c of the computer 4 in the body portion or the added file and is directed to the electronic mail address used for informing the status of a clinical specimen processing device (step S13), and transmits the electronic mail (step S14). Then, the CPU 41a completes the processes. In contrast, at step S12, when the blood smear sample forming device 2 is not shut down (No in step S12), the CPU 41a returns the sequence of processes to step S7.

Moreover, the CPU 61a of the computer 6 receives the electronic mail transmitted from the computer 4 (Yes in step S15), and stores the mail in the mail box (step S16). Upon receipt of an instruction to display the electronic mail from the technician through the input unit 63, the CPU 61a of the computer 6 accepts this instruction (Yes in step S17), and outputs an image signal used for displaying the contents of the electronic mail on the screen through the image output interface 61h so that the corresponding image is displayed on the image display unit 62 (step S18). By confirming the error information or warning information contained in the electronic mail, the technician is allowed to know the status of the blood smear sample forming device 2 so that the succeeding maintenance and control operations can be carried out smoothly.

In the status informing process of the remote control system in accordance with the present embodiment as described above, the explanation has been given by exemplifying the case in which the status (normal state, warning state, abnormal state) of the driving mechanism of the dispensation pipette 21b is determined based upon the determination criteria in which, when the number of pulses that have been given to the upward/downward driving motor 21a is located within a range from 2700 or more to 3300 or less, this case is determined as a normal state; when the number thereof is located within a range from 2400 or more to less than 2700 or within a range from 3300 or more to less than 3600, this case is determined as a warning state; and when the number thereof is located within a range from less than 2400 or 3600 or more, this case is determined as an abnormal state; however, the present invention is not intended to be limited by these, and the states of other constituent elements (for example, the dyeing solution suction discharging mechanism of the chamber 81) may be detected, or another determination criteria may be adopted.

Figure 11:
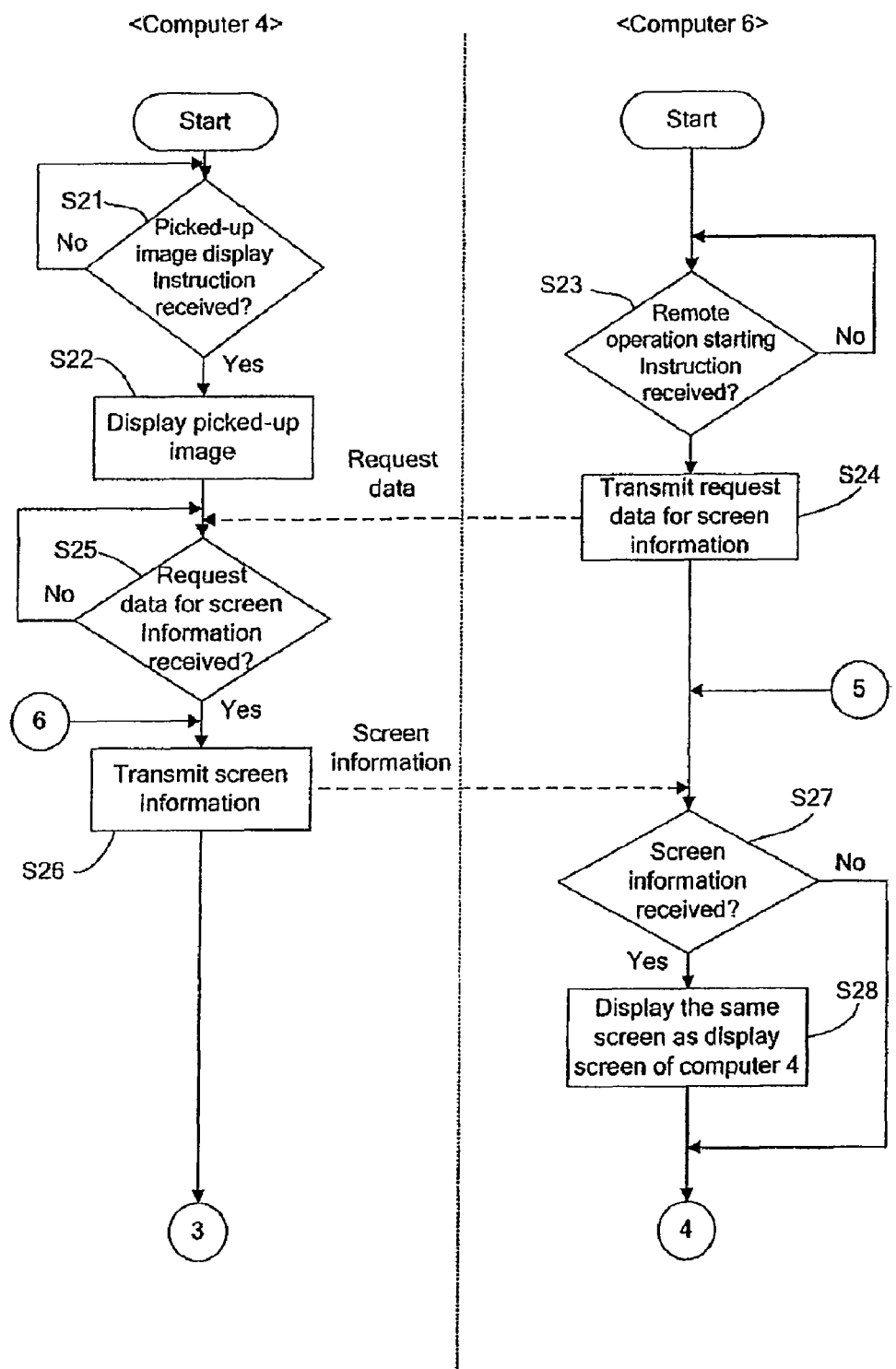
FIG. 11 is a flow chart that shows a sequence of remote supporting processes of the blood smear sample forming device in the remote control system in accordance with the embodiment of the present invention.
Figure 12:
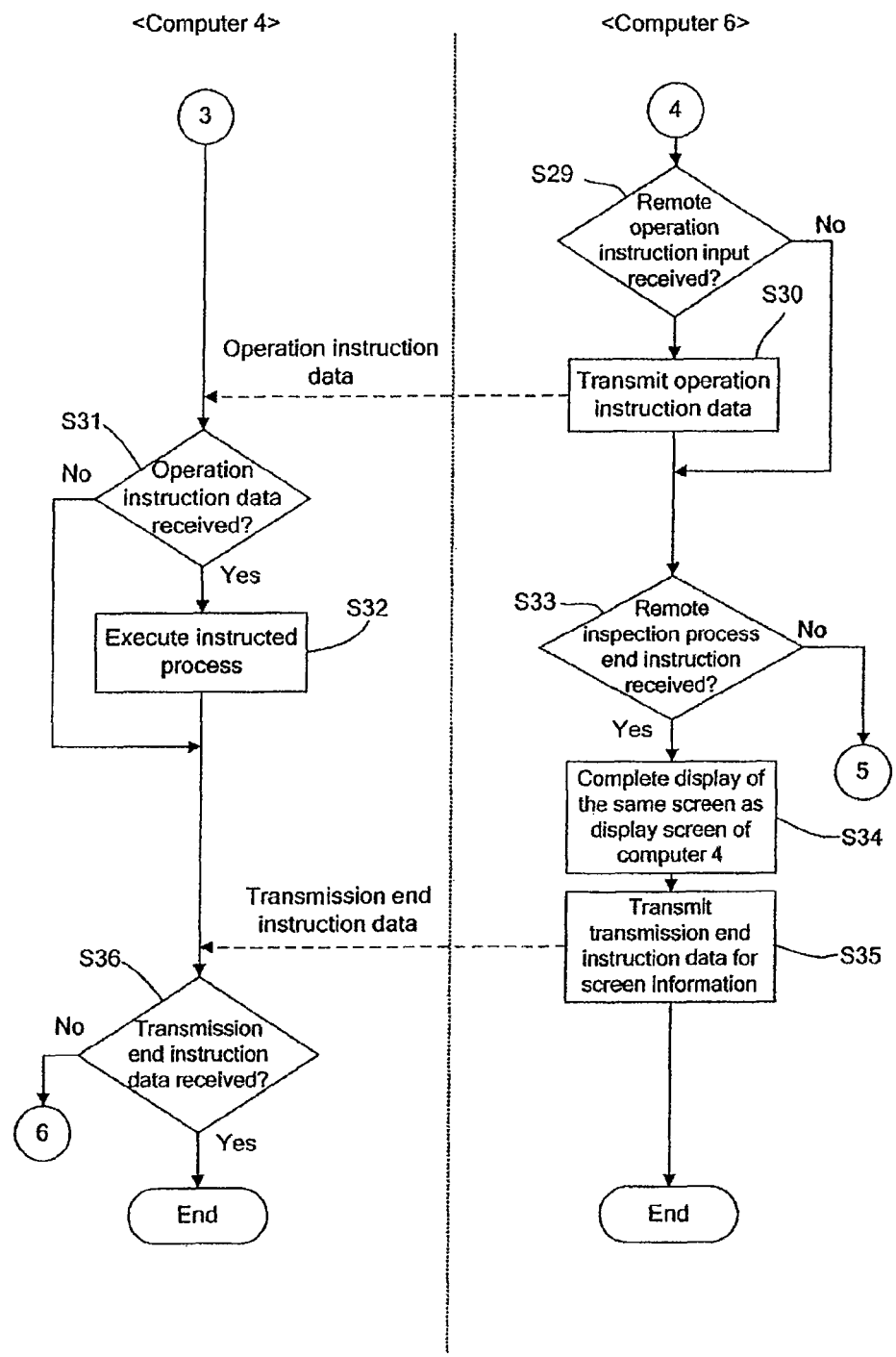
FIG. 12 is a flow chart that shows a sequence of remote supporting processes of the blood smear sample forming device in the remote control system in accordance with the embodiment of the present invention.

The following description will discuss remote supporting processes of the blood smear sample forming device 2 in the remote control system 1 in accordance with the embodiment of the present invention. FIGS. 11 and 12 show a flow chart that indicates the sequence of the remote supporting processes of the blood smear sample forming device in the remote control system in accordance with the embodiment of the present invention. As described above, for example, in the case when, upon confirmation of the error information or warning information contained in the electronic mail, the technician determines that the blood smear sample forming device 2 needs to be further confirmed in its detailed status or when the user requests an error examination, an inspection or the like to be conducted on the blood smear sample forming device 2, the technician gets in touch with the user by using a telephone or a real-time communication device, such as a television conference system using computers, and gives instructions to the user so as to direct the image pickup face of the image pickup device 5 to a subject portion for the status confirmation (for example, the driving mechanism of the dispensation pipette 21) of the blood smear sample forming device 2 and start to display the picked-up image of the image pickup device 5 by using the computer 4. Here, the user directs the image pickup face of the image pickup device 5 to the subject portion, and operates the input unit 43 of the computer 4 so that an inputting process for instructing the computer 4 to display the picked-up image of the image pickup device 5 is carried out. Upon receipt of such an instruction (Yes in step S21), the CPU 41a of the computer 4 allows the image output interface 41h to output an image signal used for displaying the picked-up image of the image pickup device 5 on the screen so that the resulting image is displayed on the image display unit 42 (step S22). Thus, a dynamic image, picked up by the image pickup device 5, is real-time displayed on the image display unit 42 of the computer 4.

Moreover, the technician operates the input unit 63 of the computer 6 so that an inputting process for instructing the computer 6 to start remote control operations on the computer 4. Upon receipt of this instruction (Yes in step S23), the CPU 61a of the computer 6 transmits data requesting for information (screen information) used for displaying the same screen as the display screen of the computer 4 through the communication interface 61g (step S24).

Upon receipt of the data requesting for the screen information through the communication interface 41g (Yes in step S25), the CPU 41a of the computer 4 simultaneously starts transmitting the screen information for the screen to be displayed on the image display unit 42 by the computer 4 (step S26). In such processes at step S26, screen information for the latest screen is transmitted in predetermined time intervals, and the transmitting process of this screen information is continued until data for instructing the transmission completion of the image information has been received from the computer 6. The CPU 61a of the computer 6 receives the screen information transmitted from the computer 4 through the communication interface 61g (Yes in step S27) so that the display screen of the computer 4 indicated by the screen information is displayed within a window (step S28). In this window, a picked-up image (dynamic image) of the image pickup device 5 is real-time displayed. This picked-up image includes an image indicating a detailed state of the subject portion for status confirmation in the blood smear sample forming device 2; thus, by confirming the picked-up image, the technician is allowed to know the detailed state of the subject portion in the blood smear sample forming device 2. Thus, without the necessity of an oral explanation on the detailed state of the blood smear sample forming device 2 by the user, the technician is allowed to directly confirm the detailed state. In a device such as the blood smear sample forming device 2 having a complex configuration, the user sometimes does not have sufficient knowledge, and in most cases, it is difficult for the user to give an oral explanation of a detailed state of the device. Therefore, in the remote control system 1 in accordance with the present invention, even in the case when the user finds it difficult to orally explain a detailed state of the device, the technician is allowed to confirm the detailed state of the device; thus, the present invention is effectively applied to such a case. Moreover, when the technician finds a minor defect in the blood smear sample forming device 2, the technician is allowed to instruct the user how to remove the defect. For example, in the case when the head of the sensor 21e is contaminated with stain with the result that the detection performance is lowered, the technician can instruct the user to remove the stain. In this manner, in the case of a minor defect in the device, since the technician is allowed to instruct the user how to remove the defect without the necessity of having to go to the user's facility, it becomes possible to easily fix the defect of the device quickly. Moreover, in the case when, upon confirmation of the picked-up image, the technician determines that the part at the defective portion should be exchanged, after required parts have been prepared by the support center, the support center can dispatch a technician to the user's facility to exchange the corresponding parts. Thus, time-consuming procedures in which a technician is once dispatched from the support center to the user's facility to confirm any defect and after required parts have been prepared by the support center, the technician is again dispatched to the user's facility so as to exchange the corresponding parts can be reduced; thus, it becomes possible to provide efficient maintenance and controlling operations, and also to achieve quick operations. Moreover, since the same picked-up image can be virtually simultaneously confirmed by the user through the computer 4 as well as by the technician through the computer 6, the two are allowed to easily communicate with each other through telephone or the like so that maintenance and control operations can be efficiently carried out quickly.

Moreover, in the case when the technician needs to carry out the operation setting of the blood smear sample forming device 2 through remote control operations, by operating the computer 4 from a remote place, the technician can input an instruction for operating the computer 4 through the input unit 63. The CPU 61a receives such an operation instruction of the computer 4 from the technician (Yes in step S29), and transmits the data corresponding to the operation instruction to the computer 4 (step S30). Upon receipt of such data (Yes in step S31), the CPU 41a of the computer 4 executes the processes thus instructed (step S32). Consequently, for example, when the technician operates the input unit 63 of the computer 6 to call for the operation setting window of the blood smear sample forming device 2 in the computer 4, or when the technician gives an instruction so as to input a setting value to the setting value input area placed on the operation setting window, the operation setting window is actually called for in the computer 4, or the setting value is actually inputted to the setting input area, so that the operation setting of the blood smear sample forming device 2 can be carried out through remote controlling operations. Here, in the present embodiment, by carrying out the same operations as those operations to be conducted on the computer 4 on the same screen as the display screen of the computer 4 displayed on the image display unit 62 of the computer 6, it is possible to remote control the computer 4. For example, in the case when the window within the screen of the computer 4 is shifted by carrying out a dragging operation with the pointer of the mouse being adjusted on the upper end of the window through operations in the input unit 43 of the computer 4, the input unit 63 of the computer 6 is operated so as to carry out a dragging operation with the pointer of the mouse being adjusted on the upper end of the window within the screen of the computer 4 displayed on the computer 6; thus, the window within the screen of the computer 4 is actually shifted. In this manner, by carrying out the same operation as the operation that is actually carried out on the computer 4, the computer 4 can be remote-controlled so that the operability of the remote operations is improved so that it becomes possible to further improve the efficiency of the maintenance and controlling operations.

Upon completion of defect-examining and inspecting operations, the technician operates the input unit 63 of the computer 6 so as to input an instruction for completing the remote supporting processes to the computer 6. Upon receipt of such an instruction (Yes in step S33), the CPU 61a of the computer 6 completes the display of the same screen as the display screen of the computer 4 (step S34), and transmits instruction data for completing the transmission of the screen information to the computer 4 (step S35), thereby completing the processes. Moreover, in the case when, at step S33, no instruction for completing the remote supporting processes is received as step S33 (No in step S33), the processes of step S27 and thereafter are repeated.

Upon receipt of the instruction data for completing the transmission of the screen information transmitted from the computer 6 (Yes in step S36), the CPU 41a of the computer 4 completes the processes; in contrast, when no instruction data is given (No in step S36), the processes of step S26 and thereafter are repeated.

In the remote supporting processes of the blood smear sample forming device 2 by the use of the remote control system 1 in accordance with the present embodiment as described above, the configuration in which a dynamic image picked up by the image pickup device 5 is displayed on the screen of the computer 6 has been explained; however, the present invention is not intended to be limited by this, and for example, another configuration may be used in which only in the case when the display screen of the computer 4 is updated (however, update of a picked-up image given by the image pickup device 5 is not included), that is, for example, in such a case when an icon or a window within the display screen of the computer 4 is shifted, the computer 4 transmits screen information indicating a new display screen to the computer 6. In this configuration, as long as the display screen of the computer 4 is not updated, the same screen as the display screen of the computer 4 that was last updated is continuously displayed on the computer 6 so that the still image picked up by the image pickup device 5 at that time is displayed on the computer 6. With this arrangement, only when the user conducts an input operation so as to update the displayed screen, the picked up image from the image pickup device 5 is transmitted from the computer 4; thus, it becomes possible to reduce the amount of communication data, and consequently to reduce a load of processes imposed on the computers 4 and 6 as well as a load imposed on the communication network NW. Moreover, when the technician requires a newly picked-up image, he or she can orally instruct the user to update the screen image so as to confirm the newly picked-up image.

In the remote supporting processes of the blood smear sample forming device 2 by the use of the remote control system 1 in accordance with the present embodiment, the configuration in which a picked-up image from the image pickup device 5 is displayed within a window used for remote-controlling the computer 4 from the computer 6 has been explained; however, the present invention is not intended to be limited by this, and another configuration in which the picked-up image from the image pickup device 5 is displayed within another window different from the window used for remote-controlling the computer 4 from the computer 6 may be used; alternatively, still another configuration in which the computer 6 is not provided with functions for carrying out the remote-control operations on the computer 4

(that is, setting for remote operations for the blood smear sample forming device 2) so that the computer 6 is allowed to receive only the picked-up image of the image pickup device 5 from the computer 4 and display the resulting image may be used.

Moreover, in the present embodiment, the blood smear sample forming device 2 is used as the subject for the remote-controlling operations; however, the present invention is not intended to be limited by this, and the subject for the remote-controlling operations may be other clinical specimen processing devices, such as a blood analyzing device for analyzing blood specimens, a urine analyzing device for analyzing urine specimens and a stool analyzing device for analyzing stool specimens.

In the present embodiment, the configuration in which the computer 4, which serves as a status setting device, is connected to the blood smear sample forming device 2 so that a picked-up image of the image pickup device 5 is transmitted to the computer 6 which serves as a control apparatus through the computer 4 has been explained; however, the present invention is not intended to be limited by this, and another configuration in which a data transmitting means is installed in the image pickup device 5 so that the picked-up image is directly transmitted from the image-pickup device 5 to the computer 6 may be used.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

The invention claimed is:

1. A remote control system comprising:
a clinical specimen processing device situated at a user facility and coupled to a communications network by a device operations controller, the clinical specimen processing device comprising first and second mechanical sections;
an image acquiring device coupled to the device operations controller and configured to acquire a processing device image of the clinical specimen processing device;
an operations communications interface coupled to the device operations controller and to the communications network, the operations communications interface having circuitry configured to transmit the processing device image and processing device status information to the communications network, the processing device status information indicating a status of each of the first and second mechanical sections and including at least one of a normal condition, a warning condition and an error condition;
first computer-readable database instructions causing the device operations controller to transmit the processing device image and the processing device status information over the operations communications interface;
a control apparatus situated at a control facility and configured to remote-control the clinical specimen processing device;
a control communications interface coupled to the control apparatus and to the communications network, the control communications interface having circuitry configured to process the processing device image and the device status information and to transmit control instructions; and
second computer-readable database instructions causing the control apparatus to transmit a selectable portion of the processing device image to a control display at the control facility and to transmit control instructions to the device operations controller over the control communications interface.

2. The remote control system of claim 1, wherein the device operations controller further comprises: circuitry in the operations communications interface that processes the control instructions; and input/output interface circuitry that initiates operations of the clinical specimen processing device based upon the control instructions.

3. The remote control system of claim 1, wherein the control communications interface further comprises circuitry that receives the processing device image and the device status information through the communications network and routes the processing device image to a control image output interface coupled to the control display.

4. The remote control system of claim 1, wherein the operations communications interface further comprises circuitry that transmits the control instructions to an operations display at the user facility through an operations image output interface.

5. The remote control system of claim 3, wherein the control image output interface comprises circuitry that displays the processing device image within a window area of the control display in real time.

6. The remote control system of claim 1, wherein the operations communications interface comprises circuitry that receives the control instructions and displays the control instructions on an operations display at the user facility.

7. The remote control system of claim 1, wherein the operations communications interface comprises circuitry that transmits control instructions to the clinical specimen processing device through the device operations controller.

8. The remote control system of claim 1, wherein the operations communications interface further comprises circuitry that transmits the device status information in predetermined time intervals to the control communication interface and continues to transmit the device status information until data instructing transmission completion is received from the control apparatus.

9. The remote control system of claim 1, wherein the operations communications interface further comprises circuitry that transmits the device status information only upon an update of the device status information by the device operations controller.

10. The remote control system of claim 1, wherein the device operations controller displays control information in a window of an operations display at the user facility and transmits the control information to the control apparatus over the operations communications interface, and the control apparatus displays the control information in a first window of the control display and the processing device image in a second window of the control apparatus.

11. The remote control system of claim 1, wherein the clinical specimen processing device comprises one of a blood smear preparing device, a blood analyzing device, a urine analyzing device, or a stool specimen analyzing device.

12. The remote control system of claim 1, wherein the device operations controller further comprises an input device configured to input control instructions; and input/output interface circuitry that initiates operations of the clinical specimen processing device based upon the input control instructions.

13. The remote control system of claim 12, wherein the device operations controller displays control information in a window of an operations display at the user facility, and the input device input the control instructions through the displayed control information.

14. The remote control system of claim 12, wherein the operations communications interface comprises circuitry that transmits the control information displayed on the operations display to the control communications interface.

15. A remote control system comprising:
a clinical specimen processing device situated at a user facility and coupled to a communications network by a device operations controller coupled to an operations input device configured to input control instructions and coupled to an operations display at the user facility;
an image acquiring device coupled to the device operations controller and configured to acquire a processing device image of the clinical specimen processing device;
an operations communications interface coupled to the device operations controller and to the communications network, the operations communications interface having circuitry that initiates operations of the clinical specimen processing device based upon the input control instructions, having circuitry that transmits the control information to the operations display configured to display the control information on the operations display, and having circuitry configured to transmit the processing device image and the displayed control information to the communications network;
first computer-readable database instructions causing the device operations controller to transmit processing device image information and the displayed control information over the operations communications interface;
a control apparatus situated at a control facility and configured to remote-control the clinical specimen processing device, the control apparatus coupled to a control input device configured to input control instructions and coupled to a control display at the control facility;
a control communications interface coupled to the control apparatus and to the communications network, the control communications interface having circuitry configured to process the processing device image and the displayed control information and to transmit input control instructions by the control input device; and
second computer-readable database instructions causing the control apparatus to display the processing device image and the displayed control information on the control display at the control facility, and to transmit the control instructions by the control input device over the control communication interface.

16. The remote control system of claim 15, wherein the operations communications interface comprises circuitry that receives the control instructions transmitted by the control apparatus, and circuitry that initiates operations of the clinical specimen processing device based upon the received control instructions.

17. The remote control system of claim 15, wherein the control image output interface comprises circuitry that displays the processing device image on the control display in real time.

18. A remote control system comprising:
a clinical specimen processing device situated at a user facility and coupled to a communications network by a device operations controller, the clinical specimen processing device comprising first and second mechanical sections;
an image acquiring device coupled to the device operations controller and configured to acquire a processing device image of the clinical specimen processing device;
an operations communications interface coupled to the device operations controller and to the communications network, the operations communications interface having circuitry configured to transmit the processing device image and processing device status information to the communications network, the processing device status information indicating a status of each of the first and second mechanical sections and including at least one of a normal condition, a warning condition and an error condition;
first computer-readable database instructions causing the device operations controller to transmit the processing device image and the processing device status information over the operations communications interface;
a control apparatus situated at a control facility, configured to remote-control the clinical specimen processing device, coupled to an input device configured to input control instructions, and comprising a memory device;
a control communications interface coupled to the control apparatus and to the communications network, the control communications interface having circuitry configured to receive the processing device image and the device status information through the communications network and to transmit the control instructions input by the input device to the communications network; and
second computer-readable database instructions causing the control apparatus to display the processing device image on a control display at the control facility, to store the device status information to the memory device and to transmit the control instructions input by the input device to the device operations controller over the control communications interface.

19. The remote control system of claim 18, wherein the second computer-readable database instructions causes the control apparatus to display the stored device status information on the control display when a display instruction is input by the input device.

20. The remote control system of claim 18, wherein the operations communications interface comprises circuitry that receives the control instructions through the control communications interface and circuitry that transmits the control instructions to the clinical specimen processing device,
wherein the control apparatus initiates operations of the clinical specimen processing device based upon the control instructions.

* * * * *